United States Patent
Sun et al.

(10) Patent No.: US 11,965,864 B1
(45) Date of Patent: Apr. 23, 2024

(54) QUANTITATIVE SOURCE APPORTIONMENT BASED ON NONTARGET HIGH-RESOLUTION MASS SPECTROMETRY (HRMS) DATA OF POLLUTION SOURCE AND POLLUTION RECEPTOR

(71) Applicant: Peking University, Beijing (CN)

(72) Inventors: Weiling Sun, Beijing (CN); Yitao Lyu, Beijing (CN); Qian Chen, Beijing (CN); Jinren Ni, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 18/449,672

(22) Filed: Aug. 14, 2023

(30) Foreign Application Priority Data

Apr. 20, 2023 (CN) .......................... 202310422604.4

(51) Int. Cl.
| | |
|---|---|
| *G01N 30/72* | (2006.01) |
| *G01N 30/86* | (2006.01) |
| *G16C 20/20* | (2019.01) |
| *G01N 30/02* | (2006.01) |

(52) U.S. Cl.
CPC ..... *G01N 30/7206* (2013.01); *G01N 30/8631* (2013.01); *G16C 20/20* (2019.02); *G01N 2030/025* (2013.01)

(58) Field of Classification Search
CPC .... G01N 30/02; G01N 30/06; G01N 30/7266; G01N 30/8631; G01N 30/8686; G01N 2030/025; G16C 20/20; Y02A 50/20
USPC .............................................................. 702/22
See application file for complete search history.

(56) References Cited

PUBLICATIONS

Chen et al. , CN 105158353 A, "Method Of Soil Polycyclic Aromatic Hydrocarbon Pollution Source And Analysis", Date Published: Dec. 16, 2015 (Year: 2015).*

* cited by examiner

*Primary Examiner* — John H Le

(57) ABSTRACT

A quantitative source apportionment method based on nontarget high-resolution mass spectrometry (HRMS) data of pollution sources and pollution receptors includes: acquiring samples of pollution sources and receptors, pre-processing samples to extract trace organic pollutants; acquiring chromatography-HRMS nontarget data; pre-processing raw data to obtain a HRMS dataset including a mass-to-charge ratio, a retention time, and a peak area; determining a source-sink relationship based on positions of pollution sources and receptors; constructing an input matrix by combining the HRMS dataset and using each sink as a group; adopting an expectation-maximization method or a Bayesian method to calculate contribution of each source based on a standardized input matrix. Beneficial effects at least include the follows. (1) The HRMS is used to acquire data to, information of the pollution source chemical fingerprint is rich and accurate; (2) contributions of different pollution sources to the receptor are quantitatively evaluated by using statistical algorithms.

5 Claims, 3 Drawing Sheets

QUANTITATIVE SOURCE APPORTIONMENT BASED ON NONTARGET HIGH-RESOLUTION MASS SPECTROMETRY (HRMS) DATA OF POLLUTION SOURCE AND POLLUTION RECEPTOR

TECHNICAL FIELD

The disclosure relates to the field of environmental monitoring technologies, and more particularly to a quantitative source apportionment based on nontarget high-resolution mass spectrometry (HRMS) data of pollution source and pollution receptor.

BACKGROUND

With implementation of prevention and control actions for air, water and soil pollution, preliminary results in pollution control are obtained, and traditional pollutants such as inhalable particulate matter, nitrogen and phosphorus nutrients, and heavy metals are effectively controlled. However, due to a continuous increase in the number of chemicals, numerous trace organic pollutants have been or are being discharged into natural environments. Most of the trace organic pollutants have features such as biotoxicity, environmental persistence and bioaccumulation, and most of them have not been effectively regulated at present stage and gradually become a key problem endangering environmental safety.

Therefore, in order to achieve pollutant reduction and risk management, it urgently needs to track the source of trace organic pollutants and develop a quantitative source apportionment technology of trace organic pollutants according to chemical features of pollution sources and various environmental samples. A nontarget screening method for trace organic pollutant analysis is developed using high-resolution mass spectrometry (HRMS). Based on the nontarget HRMS data, the contributions of various pollution sources to the trace organic pollutants of environmental samples are quantified. This provides a feasible method for quantitative source apportionment of environmental contaminants, which is important for efficient pollution control and risk management of organic pollutants.

Generally, source apportionment methods in the related art can be divided into two types. The first type often uses limited target analysis data to quantify the contributions of various pollution sources by using a multivariate statistical model such as a principal component analysis-multiple linear regression, a chemical mass balance model and a positive matrix factorization. However, it is difficult for the first type of method to quantify the contributions of pollution sources based on the nontarget HRMS dataset, and the first type of source apportionment method merely achieves quantification of types, such as a domestic pollution source, an industry source and an agricultural source, for example, methods in Chinese patent publication NO. CN112949680A, and Chinese patent publication NO. CN114544894A have these shortcomings.

The second type of source apportionment method often uses a small amount of stable isotope, heavy metals or pollution source indicators to construct a pollution source chemical fingerprint. For this type method, description for a fingerprint of the pollution source is fuzzy, incomplete, and cannot cope with a source identification and a source traceability in a situation where there are similar pollution source spectra and a large number of potential pollution source, for example, methods in Chinese patent publication NO. CN111272960B, and Chinese patent publication NO. CN108446531B have these shortcomings.

Common deficiencies of the two types of source apportionment methods in the related art are that they are difficult to accurately track and carry out targeted control, and cannot meet needs of environmental protection and management.

SUMMARY

In order to solve partial or all of technical problems in the related art, a purpose of the disclosure is to provide the following technical solutions.

An embodiment of the disclosure provides a quantitative source apportionment based on nontarget high-resolution mass spectrometry (HRMS) data of pollution sources and pollution receptors, and the method includes:
  step 1: acquiring samples of pollution sources, pollution receptors, and a background sample, and pre-processing the samples to extract trace organic pollutants from the samples;
  step 2: acquiring nontarget HRMS data of the samples obtained in step 1;
  step 3: performing data pre-processing on raw HRMS data in step 2 to obtain a dataset including a mass-to-charge ratio, a retention time, and a peak area of substance;
  step 4: determining source-sink relationship based on positions of the pollution source and the pollution receptor;
  step 5: constructing, based on the source-sink relationship obtained in step 4 and the dataset obtained in step 3, an input matrix for each sink sample, and standardizing data in the input matrix; and
  step 6: adopting an expectation-maximization method or a Bayesian method to quantitatively calculate contribution of each source sample based on a standardized input matrix.

In an embodiment, step 1 further includes:
  when the samples of the pollution source and pollution receptor are atmospheric particulate matter samples, acquiring the atmospheric particulate matter samples by using a large volume sampler and quartz fiber filter membranes, extracting non-polar organic compounds by using hexane and toluene and extracting polar organic compounds by using methanol and toluene, and concentrating the extract under nitrogen gas;
  when the samples of the pollution source and pollution receptor are water samples, extracting the water samples by using a composite solid-phase extraction (SPE) column including a lipophilic and hydrophilic balanced filler, a weak anion exchanger, a weak cation exchanger and a polar filler; sequentially eluting the SPE column by using a neutral organic solution, an acidic organic solution and an alkaline organic solution to obtain an extract, and concentrating the extract under the nitrogen gas; and
  when the samples of the pollution source and pollution receptor are soil or sediment samples, sequentially performing an shaking extraction by using a neutral organic solution, an acidic organic solution and an alkaline organic solution; enriching the extracts by using the composite SPE column including the lipophilic and hydrophilic balanced filler, the weak anion exchanger, the weak cation exchanger and the polar filler; sequentially eluting the SPE column by using a neutral organic solution, an acidic organic solution and an alkaline organic solution to obtain a final extract, and concentrating the extract under the nitrogen gas.

In an embodiment, step 2 further includes:

for the non-polar organic compounds, performing the nontarget analysis by using a gas chromatography (GC)-quadrupole time-of-flight HRMS with an electron ionization source or a chemical ionization source or a GC-Orbitrap HRMS with the electron ionization source or the chemical ionization source; and for the polar organic compounds and water-soluble compounds, performing the nontarget analysis by using an ultra-high-performance liquid chromatography (LC)-quadrupole time-of-flight HRMS with an electrospray ion source or an ultra-high-performance LC-Orbitrap HRMS with the electrospray ion source.

In an embodiment, step 3 further includes: for a LC-HRMS, during performing peak extraction and peak alignment, setting a primary mass spectrometry (MS) permissible mass deviation and a secondary mass spectrometry ($MS^2$) permissible mass deviation, and extracting peaks of each sample within a range of permissible mass deviation for each MS and MS 2 to merge into one peak; during performing peak elimination, setting a minimum extraction threshold and performing a blank deduction, and eliminating peaks with signal intensity smaller than the threshold and peaks existed in the blank sample.

In an embodiment, step 4 further includes: taking each remaining sample other than a background sample and the samples of the pollution source as a sink sample, one sink sample corresponding to one group, and determining the source samples of each sink sample.

In an embodiment, step 5 further includes: constructing a sink sample vector and a source sample vector for each group based on the dataset obtained in step 3, representing a single sink sample by using a vector x, where a formula of x is $x=(x_1, \ldots, x_j, \ldots, x_N)$, $x_j$ represents a signal intensity of a j-th substance, N represents the number of all substance types in the dataset obtained in step 3; and representing a known source sample i of the sink sample x by using a vector $y_i$, where a formula of $y_i$ is $y_i=y_{i1}, \ldots, y_{ij}, \ldots, y_{iN}$, $y_{ij}$ represents a signal intensity of a j-th substance in the source sample i and $1 \leq i \leq K$, K represents the number of all known source samples of the sink sample x, and the sink sample x includes an unknown source sample, that is a K+1-th source sample.

In an embodiment, the step 5 further includes: constructing the input matrix $(x^T, y_1^T, y_2^T, \ldots, y_K^T)$, where in a situation that the input matrix has a missing value, populating a value 0 into the input matrix, and standardizing the input matrix.

In an embodiment, the standardization of the input matrix includes: z-score standardization, or [0,1] standardization to obtain a standardized input matrix.

In an embodiment, step 6 further includes: substituting the vector x of the sink sample and the vector $y_i$ of the source sample i in the expectation-maximization method, including randomly assigning a value for contribution $\alpha_i$ of the sink sample x, substituting the input matrix $(x^T, y_1^T, y_2^T, \ldots, y_K^T)$ in the expectation-maximization method to iterate the contribution $\alpha_i$ until convergence or reaching a maximum number of iterations.

In an embodiment, the step 6 further includes: substituting the vector x of the sink sample and the vector $y_i$ of the source sample i in the Bayesian method, including initializing the contribution $\alpha_i$ by using a random source environment assignment, iteratively calculating the contribution $\alpha_i$ to update each vector according to a conditional distribution, and calculating a posterior probability until convergence or reaching the maximum number of iterations.

Compared with the related art, beneficial effects of the disclosure at least include the follows.

(1) The HRMS is used to acquire pollution source chemical fingerprint, information of the pollution source chemical fingerprint is rich and accurate, which applies to pollution source apportionment of various environment mediums such as air, water and soil; (2) contributions of different pollution sources to the pollution receptor can be quantitatively evaluated by using multiple statistical algorithms.

More specifically, HRMS nontarget analysis technology used in the disclosure is an advanced technology for monitoring and analyzing the trace organic pollutants at present, which no need to identify detected substance, contribution of each pollution source can be quantitatively apportioned based on the nontarget HRMS data of known pollution sources and pollution receptors; information of the pollution source chemical fingerprint is complete and rich, which is beneficial for dealing with complex and diverse pollution sources.

The disclosure first proposes a quantitative method for contributions of the pollution sources based on the HRMS dataset in a field of environmental pollutant source apportionment, which can achieve a fast and accurate source apportionment under a situation that there are similar pollution source chemical fingerprint and a large number of potential pollution sources.

DETAILED DESCRIPTION OF EMBODIMENTS

Technical solutions in embodiments of the disclosure will be clearly and completely described in conjunction with drawings in the embodiments of the disclosure in the follows to make purposes, technical solutions and advantages of the disclosure clearer. The described embodiments are merely some embodiments of the disclosure, not all of them. Based on spirit of the disclosure, all other embodiments obtained by those skilled in the art without creative works fall within a scope of protection of the disclosure.

Figure 1:
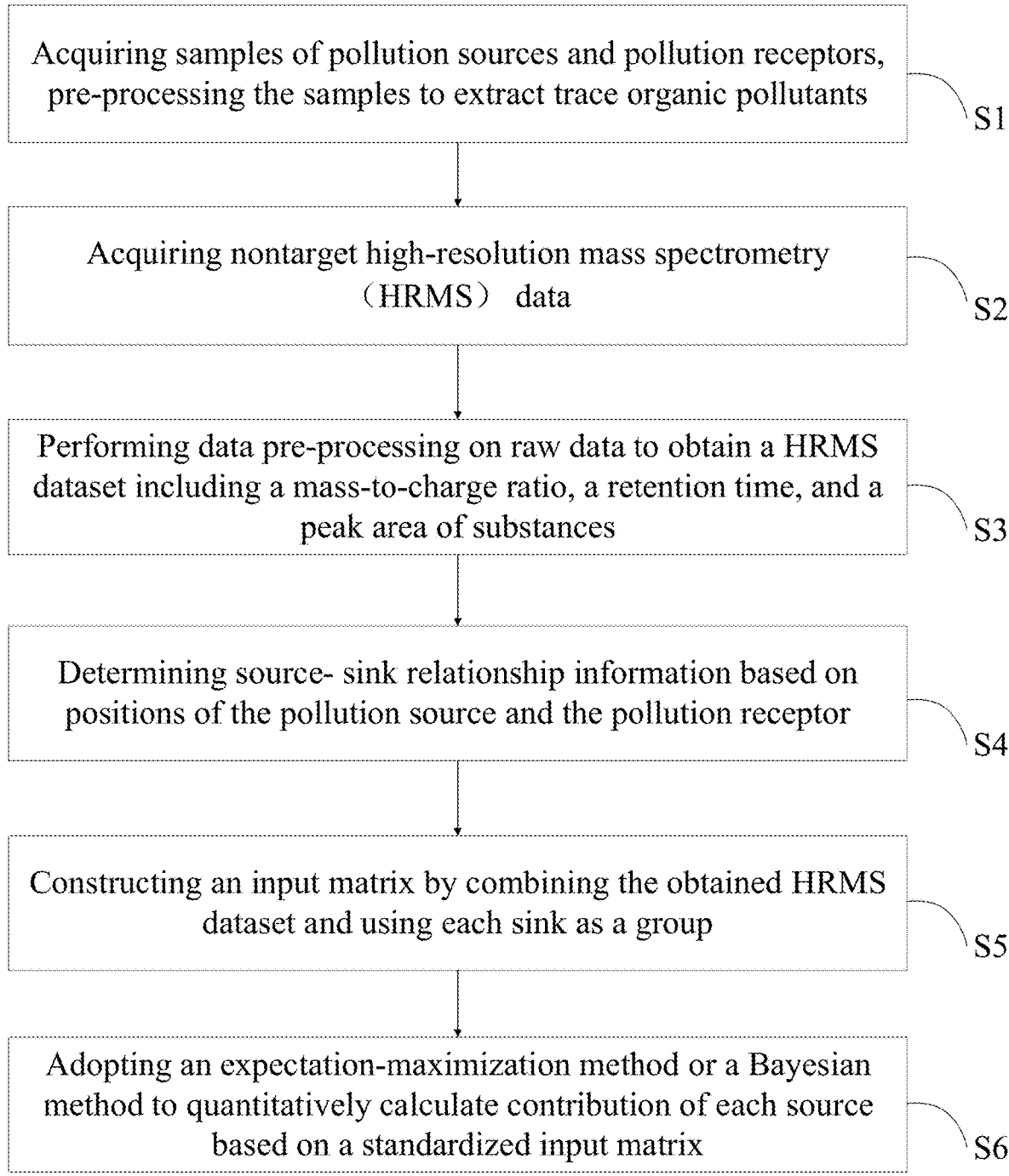
FIG. 1 illustrates a flowchart of a quantitative source apportionment method based on nontarget high-resolution mass spectrometry (HRMS) data of pollution sources and pollution receptors according to an embodiment of the disclosure.

As shown in FIG. 1, the embodiment of the disclosure provides a quantitative source apportionment method based on nontarget high-resolution mass spectrometry (HRMS) data of pollution sources and pollution receptors, and the method includes the following steps 1-6.

In step 1, pollution source samples, pollution receptor samples and a background sample are acquired, and the samples (i.e., the pollution source sample, the pollution receptor sample and the background sample) are pre-processed to extract trace organic pollutants from the samples.

Specifically, one of air, water, soil or sediment samples of pollution sources and pollution receptors are acquired according to the distribution feature of the target pollution sources to obtain the pollution source samples and the pollution receptor samples, and the samples are pre-processed to reach a purpose of enrichment and purification. Specifically, an atmospheric particulate matter sample is acquired by using a large volume sampler and a quartz fiber filter membrane, and a pre-processing process including shaking extraction, membrane filtration, addition of internal standards, nitrogen blowing, and constant volume is performed on the atmospheric particulate matter sample; a water sample is acquired by using a brown glass container, and a pre-processing process including addition of the internal standard, membrane filtration, solid phase extraction, elution, nitrogen blowing, and constant volume is performed on the water sample; a soil or sediment sample is acquired by using an aluminum box, and a pre-processing process including freeze-drying, grinding and sieving, addition of internal standards, shaking extraction, dilution, solid-phase extraction, elution, nitrogen blowing, and constant volume is performed on the soil or sediment sample.

In an embodiment, during the extraction of trace organic pollutants, when the samples of the pollution source and the pollution receptor are acquired from air, using the large volume sampler and the quartz fiber filter membrane, and non-polar organic compounds are extracted by using hexane and toluene and polar organic compounds are extracted by using methanol and toluene to thus obtain an extract solution, the extract solution is merged, filtered and concentrated under nitrogen gas.

When the samples of the pollution source and the pollution receptor are acquired from a river with a sewage discharges, sewage samples and river water samples are acquired by using the brown glass container, then particulate matter in the samples (i.e., sewage discharge sample and the river water sample) are removed by using the membrane filtration, during the solid phase extraction (SPE), a composite SPE column including a lipophilic and hydrophilic balanced filler, a weak anion exchanger, a weak cation exchanger and a polar filler are used to extract the samples; during the elution, neutral organic solution, acidic organic solution and alkaline organic solution are used to sequentially elute the SPE column to thus ensure a good extraction effect for organic micro pollutants with different polarity and different acidity and alkalinity.

When the samples of the pollution source and the pollution receptor are soil or sediment samples, neutral organic solution, acidic organic solution and alkaline organic solution are used to sequentially perform the shaking extraction; during SPE, the composite SPE column including the lipophilic and hydrophilic balanced filler, the weak anion exchanger, the weak cation exchanger and the polar filler is used to extract the soil or sediment samples; during the elution, neutral organic solution, acidic organic solution and alkaline organic solution are used to sequentially elute the composite SPE column to thus ensure the good extraction effect for the organic micro pollutants with different polarity and different acidity and alkalinity.

Specifically, the disclosure applies to treatment of various pollution sources with significant differences and multiple sources such as life, agriculture, transportation, and industry.

In an embodiment, in order to analyze pollution contribution of a certain river sewage treatment plant to downstream water, 4 samples are acquired, and the 4 samples are 1 water outlet sample of the sewage treatment plant, 1 upstream water sample of the water outlet, and 2 downstream water samples of the water outlet, respectively. Specifically, distances between 2 sampling points of downstream water of the water outlet and the water outlet are different. As shown in the following table.

TABLE 1

| Sampling example | | |
|---|---|---|
| | Sampling point | description |
| Sample 1 | Upstream of water outlet of sewage treatment plant | Background sample |
| Sample 2 | water outlet of sewage treatment plant | Pollution source |
| Sample 3 | Position 1 of downstream of water outlet of sewage treatment plant | Distances from positions 1 and 2 to the water outlet are different |
| Sample 4 | Position 2 of downstream of water outlet of sewage treatment plant | |
| Sample 5 | Process blank sample | |

In step 2, nontarget HRMS data is acquired of the samples obtained in step 1.

Specifically, for the nonpolar organic compounds, nontarget analysis is performed by using a gas chromatography (GC)-quadrupole time-of-flight HRMS with an electron ionization source or a chemical ionization source or a GC-Orbitrap HRMS with the electron ionization source or the chemical ionization source.

In an embodiment, a capillary column is used by GC in a programmed heating mode to separate compounds.

For the polar organic compounds and water-soluble compounds, the nontarget analysis is performed by using an ultra-high-performance liquid chromatography (LC)-quadrupole time-of-flight HRMS with an electrospray ion source or an ultra-high-performance liquid chromatography (LC)-Orbitrap HRMS with the electrospray ion source.

In an embodiment, a reverse chromatography column is used by ultra-high performance LC in a gradient elution mode to separate the sample, a full scan of MS and a data-dependent acquisition (DDA) of $MS^2$ are respectively performed by a HRMS in positive and negative modes.

A positive and negative mode calibration is performed to make a mass accuracy deviation smaller than 2 parts per million (ppm) before each analysis. In a situation that a mass spectrometry resolution is 140000, full scan of MS data within a range of mass-to-charge ratio 100-1500 is obtained. In a situation that the mass spectrometry resolution is 17500, $MS^2$ data is acquired. Gradient normalized collision energy is used to obtain $MS^2$ data with data dependency.

In step 3, data pre-processing is performed on raw HRMS data obtained through the nontarget analysis in step 2 to obtain a HRMS dataset including a mass-to-charge ratio, a retention time, and a peak area of substances.

Specifically, commercial mass spectrometry software is used to perform peak extraction, peak alignment, peak combination and peak elimination on raw mass spectrometry data. For example, during performing the peak extraction and the peak alignment, a MS permissible mass deviation and a $MS^2$ permissible mass deviation are set, and peaks of each sample within a range of permissible mass deviations for each MS and $MS^2$ are extracted to merge into one peak; and during performing the peak elimination, a minimum extraction threshold is set and a blank deduction is performed, and peaks with a signal intensity smaller than the threshold and peaks existed in the blank sample are eliminated.

The HRMS dataset including the substance mass-to-charge ratio, the retention time, and the peak area is obtained through the data pre-processing.

In step 4, source-sink relationship is determined according to positions of the pollution sources and the pollution receptors.

A source-sink relationship is determined according to a relationship of water flow direction and geographical location of each pollution source and pollution receptor. For example, but not limited to upstream and downstream, and altitude to determine the source-sink relationship. A certain river flows through the water outlets of two sewage treatment plants a and b in sequence, that a and b are two pollution sources, and a water sample in upstream of a is not affected by a and b; in downstream of a, a water sample in upstream of b is a sink of a and upstream water; and a water sample in downstream of b is a sink of a, b and the upstream water.

Follow the example from the step 1, the sample 1 is a background sample, the sample 2 is a pollution source sample, thus drawing a table for the source-sink relationship shown in follows, in the table, id represents a group order number, in addition to the background sample 1 and the pollution source sample 2, each remaining sink sample and source sample of the remaining sink sample are one group, SourceSink represents a sink or a source in the group, SampleID represents an order number. It can be understood that the source and the sink are input as a class variable, the source is recorded as "Source", and the sink is recorded as "Sink"; the source-sink relationship is also input as a class variable, the sink and sources that have an impact on the sink are marked as a same number, and the source can be repeatedly input. The source-sink relationship for this example is provided in the following table.

TABLE 2

Table for the source-sink relationship

| Sample ID | | SourceSink | id |
|---|---|---|---|
| Sample 3 | 1 | Sink | 1 |
| Sample 1 | 2 | Source | 1 |
| Sample 2 | 3 | Source | 1 |
| Sample 4 | 4 | Sink | 2 |
| Sample 1 | 5 | Source | 2 |
| Sample 2 | 6 | Source | 2 |

It can be understood that in the above table, in addition to the sample 1 and the pollution source sample 2, the samples 3 and 4 are used as the sinks to divide two groups, that is id=1 and 2. In a situation that id=1, in a first group, the sample 3 is the sink and marked as Sink, the sample 1 and the sample 2 in upstream of the sample 3 are the sources of the sample 3 and marked as Source. In a situation that id=2, in a second group, the sample 4 is the sink and marked as Sink, the sample 1 and the sample 2 in upstream of the sample 4 are the sources of the sample 4 and marked as Source.

In step 5, an input matrix is constructed based on the source-sink relationship obtained in step 4 and the HRMS dataset obtained in step 3 for each group of the sink sample, and mass spectrometry data of the input matrix is standardized.

Specifically, a sink sample vector and a source sample vector are constructed for each group based on the HRMS dataset obtained in step 3. More specifically, a vector x is used to represent the single sink sample, and a formula of x is $x=(x_1, \ldots, x_j, \ldots, x_N)$, $x_j$ represents a signal intensity of a j-th substance, N represents the number of all substance types in the HRMS dataset obtained in step 3. A vector $y_i$ is used to represent a known source sample i of the sink sample x, a formula of $y_i$ is $y_i=y_{i1}, \ldots, y_{ij}, \ldots, y_{iN}$, $y_{ij}$ represents a signal intensity of a j-th substance in the source sample i and $1 \leq i \leq K$, K represents the number of all known source samples of the sink sample x, and the sink sample x includes an unknown source sample, that is a K+1-th source sample.

$\alpha_i$ is used to represent a contribution of the source sample i to the sink sample x, obviously, $\Sigma_{j=1}^{K+1}\alpha_i=1$, for each of the sink sample, a sum of contribution of all source samples is 1, and the all source samples include K known source samples and K+1-th unknown source sample.

The input matrix $(x^T, y_1^T, y_2^T, \ldots, y_K^T)$ is constructed, in a situation that the input matrix has a missing value, a value 0 is populated into the input matrix, and the input matrix is standardized. In an embodiment, standardizing includes z-score standardization, or [0,1] standardization.

In step 6, an expectation-maximization method or a Bayesian method is adopted to quantitatively calculate the contribution of each source based on the standardized input matrix.

In an embodiment, the vector x of the sink sample x and the vector $y_i$ of the source sample i are substituted in the expectation-maximization method, and the step includes the following steps, a value is randomly assigned for contribution $\alpha_i$ of the sink sample x, for example, but not limited to evenly assign for the contribution $\alpha_i$, the contribution $\alpha_i$ and the input matrix $(x^T, y_1^T, y_2^T, \ldots, y_K^T)$ are substituted in the expectation-maximization method to calculate a maximum likelihood function, and the contribution $\alpha_i$ is iterated until convergence or a maximum number of iterations is reached.

In an embodiment, based on the Bayesian method, and a data input way of the Bayesian method is similar to the expectation-maximization method.

The contribution $\alpha_i$ is initialized by using a random source environment assignment, for example, but not limited to evenly assign for the contribution $\alpha_i$, the contribution $\alpha_i$ is iteratively calculated to update each vector according to a conditional distribution, and a posterior probability is calculated until convergence or the maximum number of iterations is reached.

In an exemplary embodiment, the contribution of each of the sources obtained from the step 6 is sent to the source (e.g., the sewage treatment plant), and the source performs sewage treatment thereby achieves the purpose of pollution prevention and control.

The disclosure will be further described by the following embodiment to make the disclosure clearer.

Embodiment 1: An Apportionment for Pollution Contribution of the Certain River Sewage Treatment Plant to the Downstream Water (1) One water sample in the water outlet of the sewage treatment plant, one water sample in the upstream of the sewage treatment plant and two water samples in different positions of the downstream of the sewage treatment plant are acquired, and four environment samples are obtained by performing membrane filtration, solid phase extraction, elution, nitrogen blowing, and constant volume. And a process blank sample is prepared.

(2) A data acquisition with positive and negative modes of the four environment samples and one blank sample are implemented by using an ultra-high-performance LC-Orbitrap HRMS.

Figure 2:
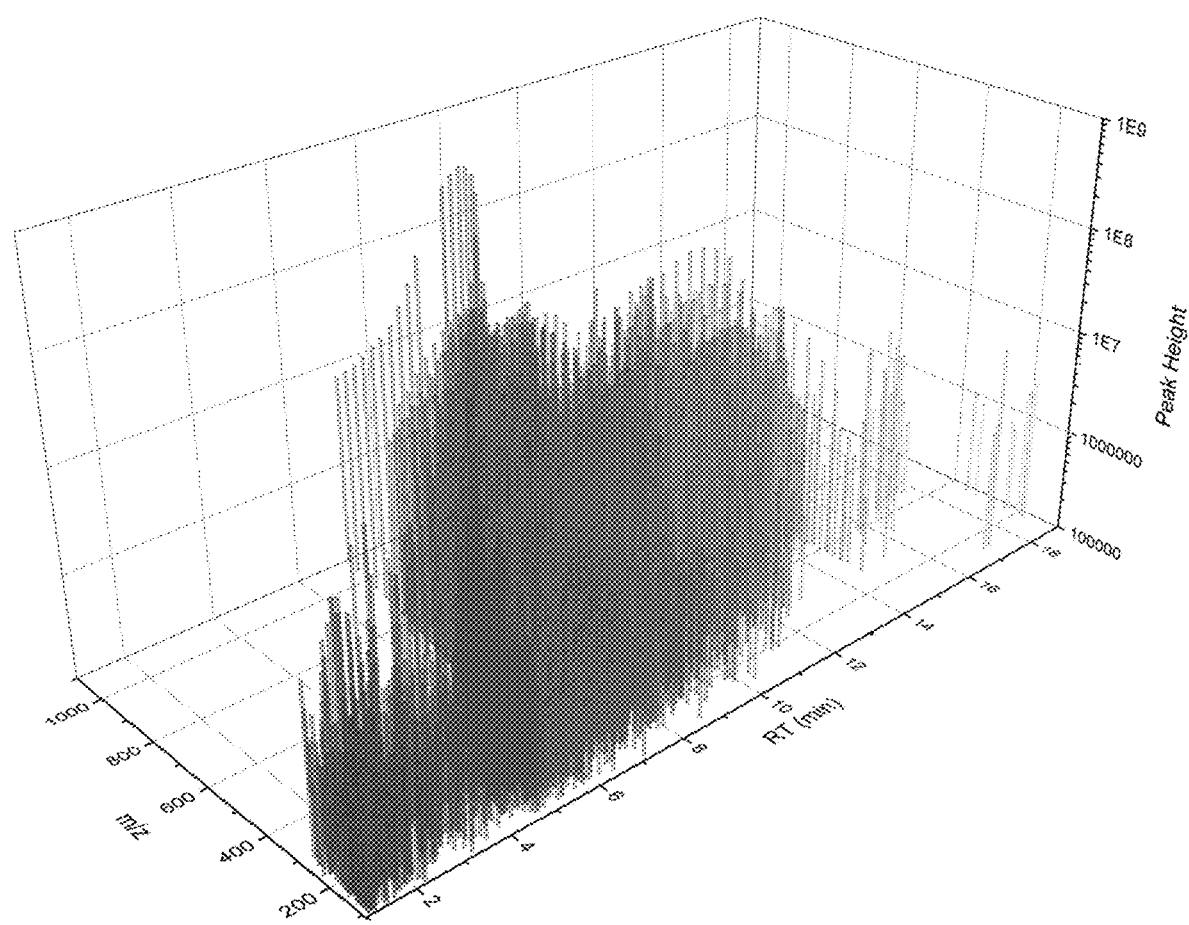
FIG. 2 illustrates a schematic diagram of a full scan mass spectrometry of a pollution source according to an embodiment of the disclosure.
Figure 3:
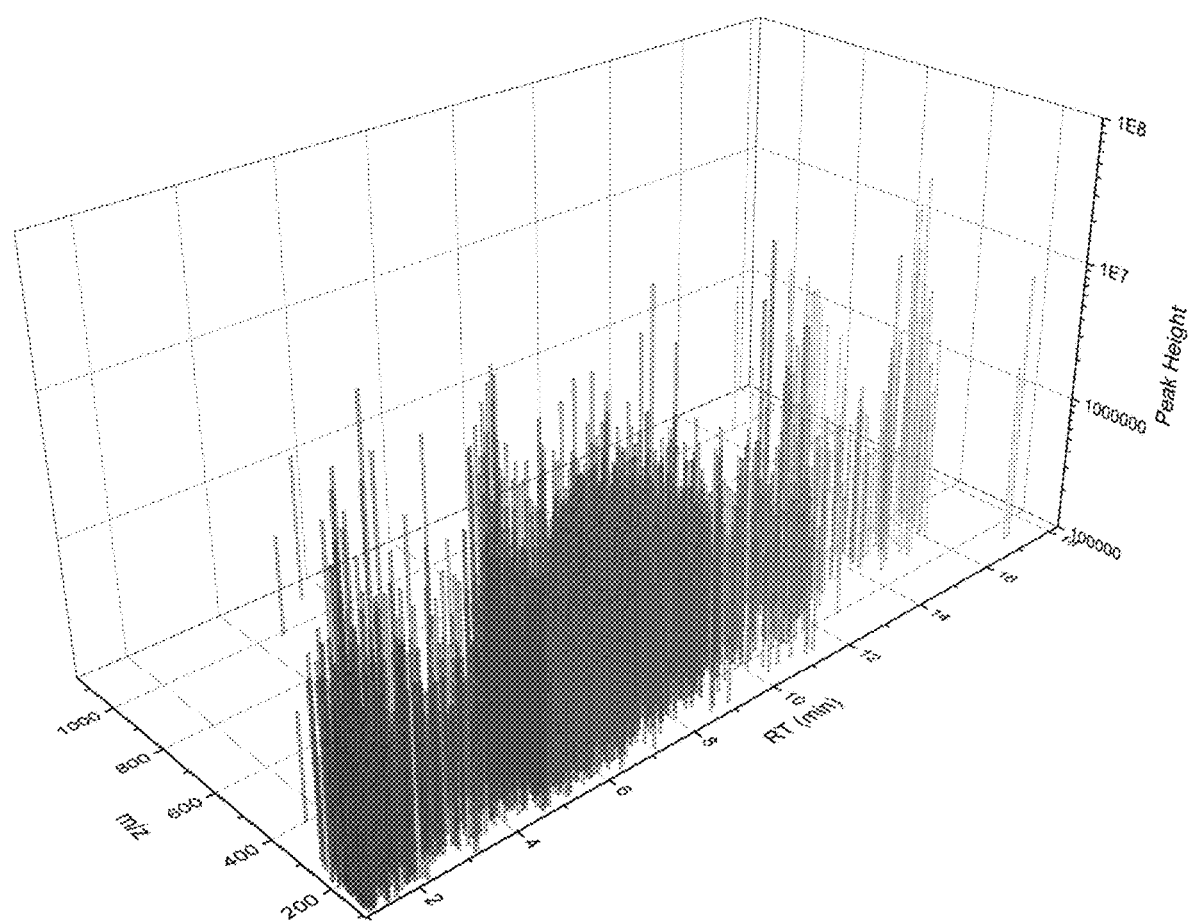
FIG. 3 illustrates a schematic diagram of a scan mass spectrometry of a receptor sample according to an embodiment of the disclosure.

(3) Raw mass spectrometry data is pre-processed by using a commercial mass spectrometry software to obtain the HRMS dataset. Specifically, 6168 peaks are obtained in the positive mode, 2266 peaks are obtained in the negative mode, a full scan mass spectrometry of the pollution samples and one of the pollution receptor samples are shown in FIG. 2 and FIG. 3, partial HRMS dataset is shown in Table 3.

TABLE 3

| | | | | HRMS dataset (part) | | | |
|---|---|---|---|---|---|---|---|
| Number | Retention time (min) | Mass-to-charge ratio | Signal-to-noise ratio | Pollution source (simple 2) | Upstream (sample 1) | Receptor 1 (sample 3) | Receptor 2 (sample 4) |
| 1 | 1.73 | 100.03983 | 37.23 | 0 | 0 | 0 | 0 |
| 2 | 1.261 | 100.0763 | 212.26 | 0 | 0 | 0 | 0 |
| 3 | 2.234 | 100.11259 | 94.76 | 0 | 0 | 0 | 4395262 |
| 4 | 1.201 | 101.00887 | 77.8 | 508766 | 560688 | 5498764 | 2696597 |
| 5 | 1.23 | 101.00892 | 56.56 | 508766 | 560688 | 5541182 | 2285930 |
| 6 | 3.192 | 101.06017 | 14.12 | 0 | 747047.5 | 0 | 0 |
| 7 | 1.1 | 101.10787 | 437.97 | 526800.5 | 0 | 0 | 0 |
| 8 | 1.62 | 101.1079 | 101.25 | 1056902 | 944683 | 1877489 | 1403955 |
| 9 | 1.446 | 101.10799 | 109.99 | 766562.5 | 659690 | 902680 | 948481.5 |
| 10 | 1.479 | 102.12807 | 54662.66 | 1.08E+08 | 1.29E+08 | 65944428 | 1.25E+08 |
| 11 | 1.167 | 102.1283 | 903.48 | 6286083 | 10335557 | 1513530 | 3274250 |
| 12 | 1.214 | 102.97073 | 47.33 | 0 | 532363 | 3493744 | 1607667 |
| 13 | 1.101 | 103.03302 | 86.62 | 3934102 | 3321687 | 2959865 | 4291936 |
| 14 | 1.835 | 103.08708 | 20.14 | 0 | 0 | 0 | 0 |
| 15 | 1.662 | 104.11874 | 119.99 | 0 | 0 | 0 | 0 |
| 16 | 7.067 | 105.03391 | 89.09 | 0 | 0 | 0 | 0 |
| 17 | 1.92 | 105.0374 | 14.01 | 0 | 0 | 627433 | 0 |
| 18 | 3.264 | 105.0704 | 27.06 | 0 | 0 | 0 | 2670400 |
| 19 | 5.62 | 106.03258 | 98.35 | 0 | 0 | 0 | 0 |
| 20 | 2.067 | 107.04964 | 18.94 | 0 | 0 | 0 | 1098047 |
| 21 | 3.052 | 107.04964 | 9.72 | 0 | 0 | 0 | 736270 |
| 22 | 5.549 | 107.04966 | 47.49 | 0 | 0 | 0 | 3860319 |
| 23 | 5.13 | 107.04967 | 31.52 | 0 | 0 | 0 | 2723811 |
| 24 | 3.694 | 107.04967 | 15.89 | 0 | 0 | 0 | 1375473 |
| 25 | 1.73 | 107.04968 | 66.13 | 0 | 0 | 0 | 5628304 |
| 26 | 4.843 | 107.04971 | 16.21 | 0 | 0 | 0 | 1236862 |
| 27 | 6.041 | 107.0707 | 27.41 | 0 | 0 | 0 | 0 |
| 28 | 7.166 | 107.08593 | 18.69 | 1450022 | 1666468 | 1336332 | 1589364 |
| 29 | 6.381 | 107.08598 | 13.33 | 603571.5 | 918711 | 697879.5 | 842883 |
| 30 | 4.671 | 107.08604 | 15.17 | 0 | 619567.5 | 0 | 796919.5 |
| 31 | 1.206 | 108.08129 | 88.69 | 0 | 0 | 1674546 | 1802673 |
| 32 | 1.313 | 108.08132 | 1136.23 | 0 | 0 | 1675492 | 2626851 |
| 33 | 5.226 | 109.06522 | 15.07 | 1002708 | 1072616 | 818960.5 | 1116876 |
| 34 | 4.752 | 109.06526 | 32.36 | 0 | 0 | 0 | 0 |
| 35 | 1.225 | 109.07642 | 21.46 | 1248606 | 1086422 | 1182010 | 1383185 |
| 36 | 1.453 | 109.07645 | 20.84 | 1354722 | 1044978 | 1305941 | 1282464 |
| 37 | 1.524 | 109.07648 | 18.93 | 1094279 | 856636 | 1506291 | 828746 |
| 38 | 1.213 | 110.06042 | 62.67 | 884584.5 | 709589.5 | 0 | 1365577 |
| 39 | 5.235 | 110.08427 | 32.52 | 0 | 0 | 753330.5 | 0 |
| 40 | 3.209 | 110.08437 | 28.59 | 0 | 0 | 611478 | 0 |
| 41 | 4.829 | 111.04451 | 10.24 | 823763.5 | 862681 | 561988 | 679752 |
| 42 | 2.23 | 111.09196 | 532.29 | 2268131 | 1903639 | 87353224 | 724443 |
| 43 | 1.706 | 111.09198 | 3546.08 | 51482260 | 49116020 | 6.19E+08 | 6198006 |
| 44 | 1.788 | 111.09205 | 18068.92 | 8749248 | 8942856 | 87023164 | 580941 |
| 45 | 1.287 | 111.09206 | 25.51 | 0 | 0 | 0 | 0 |
| 46 | 2.324 | 111.0921 | 61.76 | 0 | 0 | 7238814 | 0 |
| 47 | 1.198 | 111.09214 | 15.68 | 802693.5 | 612940.5 | 542298 | 638580 |
| 48 | 1.373 | 111.0922 | 46.67 | 645446 | 0 | 681689.5 | 3286654 |
| 49 | 10.515 | 111.11716 | 124.16 | 0 | 0 | 0 | 0 |
| 50 | 1.705 | 111.11725 | 12.79 | 0 | 0 | 0 | 0 |
| 51 | 10.65 | 111.11725 | 45.18 | 0 | 747236 | 3948730 | 0 |
| 52 | 4.347 | 112.07608 | 78.61 | 0 | 0 | 1224724 | 0 |
| 53 | 4.163 | 112.07609 | 19.98 | 0 | 591476.5 | 0 | 0 |
| 54 | 1.149 | 112.0873 | 9442.11 | 26450500 | 19959870 | 44797550 | 60787316 |
| 55 | 2.073 | 113.02371 | 150.78 | 5906018 | 5842688 | 0 | 0 |
| 56 | 2.166 | 113.02383 | 162.77 | 2819993 | 2783163 | 2381601 | 9460416 |
| 57 | 6.477 | 113.06004 | 35.48 | 689176.5 | 1483546 | 1529597 | 1153916 |
| 58 | 3.03 | 114.05538 | 28.47 | 0 | 0 | 0 | 0 |
| 59 | 4.757 | 114.09159 | 904.37 | 22525995 | 15792631 | 6995564 | 14062300 |
| 60 | 1.299 | 114.09177 | 24.87 | 1300346 | 1627086 | 1914282 | 1140175 |
| 61 | 1.733 | 115.03935 | 65.9 | 1475261 | 2369686 | 0 | 0 |
| 62 | 1.105 | 115.05059 | 38.34 | 0 | 591359.5 | 614841.5 | 1794873 |
| 63 | 1.841 | 115.12337 | 13.02 | 0 | 0 | 0 | 0 |
| 64 | 1.798 | 116.01692 | 196.84 | 0 | 0 | 0 | 0 |
| 65 | 1.899 | 116.07102 | 608.53 | 1384267 | 2757071 | 6534789 | 756557 |
| 66 | 1.519 | 116.10736 | 22.06 | 0 | 0 | 618146.5 | 0 |
| 67 | 1.09 | 116.11856 | 499.03 | 850102 | 1026627 | 1058620 | 0 |
| 68 | 4.902 | 117.05502 | 9.13 | 0 | 0 | 0 | 0 |
| 69 | 3.651 | 117.05503 | 9.36 | 0 | 0 | 0 | 0 |
| 70 | 1.172 | 117.07749 | 616.2 | 2999629 | 2851015 | 3406620 | 7941517 |
| 71 | 1.178 | 117.10255 | 40.43 | 0 | 0 | 0 | 0 |
| 72 | 5.032 | 117.10265 | 21.26 | 0 | 0 | 0 | 0 |
| 73 | 1.209 | 118.08656 | 25.18 | 3091129 | 3038975 | 1456484 | 2918842 |
| 74 | 5.331 | 118.08661 | 13.5 | 1501249 | 1443867 | 1350599 | 1552284 |
| 75 | 1.551 | 118.08662 | 20.05 | 3584802 | 3320036 | 2430653 | 3340092 |

TABLE 3-continued

HRMS dataset (part)

| Number | Retention time (min) | Mass-to-charge ratio | Signal-to-noise ratio | Pollution source (simple 2) | Upstream (sample 1) | Receptor 1 (sample 3) | Receptor 2 (sample 4) |
|---|---|---|---|---|---|---|---|
| 76 | 1.313 | 118.08665 | 29.38 | 4179586 | 4208247 | 2496413 | 2977822 |
| 77 | 2.069 | 118.08666 | 8.3 | 3500275 | 3438207 | 3119969 | 3530017 |
| 78 | 5.232 | 118.08667 | 9.76 | 1510830 | 1553688 | 1441599 | 1702491 |
| 79 | 4.699 | 118.08668 | 8.78 | 2268764 | 2172506 | 2059817 | 2211040 |
| 80 | 1.983 | 118.08677 | 21.39 | 3582650 | 3514329 | 3272559 | 3393416 |
| 81 | 1.966 | 118.12296 | 132.59 | 10912280 | 11152690 | 19519717 | 10120874 |
| 82 | 1.195 | 118.12312 | 213.99 | 0 | 0 | 0 | 0 |
| 83 | 1.22 | 119.01937 | 76.06 | 1284835 | 1441495 | 13846045 | 5473206 |
| 84 | 1.935 | 119.06073 | 21.01 | 1660960 | 1435818 | 1393838 | 3037363 |
| 85 | 9.071 | 119.08582 | 4.61 | 528932 | 601582 | 0 | 557309 |
| 86 | 7.217 | 119.994 | 523.36 | 0 | 0 | 0 | 0 |
| 87 | 6.428 | 120.04826 | 955.85 | 0 | 0 | 0 | 0 |
| 88 | 1.11 | 120.05591 | 44.31 | 1254490 | 1664622 | 0 | 690859 |
| 89 | 5.64 | 120.05599 | 79.25 | 2142710 | 2397370 | 1012305 | 1021984 |
| 90 | 2.629 | 120.08112 | 30.48 | 0 | 0 | 0 | 0 |
| 91 | 8.656 | 121.02863 | 49.71 | 2181622 | 2556180 | 3790974 | 3990631 |
| 92 | 8.295 | 121.02864 | 25.92 | 0 | 0 | 0 | 0 |
| 93 | 1.277 | 121.04002 | 783.03 | 9995466 | 4511851 | 2274562 | 4424966 |
| 94 | 1.615 | 121.07641 | 8.6 | 0 | 0 | 0 | 0 |
| 95 | 5.822 | 121.10149 | 18.61 | 1010145 | 1140168 | 1196305 | 1190673 |
| 96 | 6.545 | 122.00962 | 179.91 | 0 | 0 | 0 | 0 |
| 97 | 2.484 | 122.06036 | 13.88 | 0 | 0 | 503304.5 | 562327 |
| 98 | 5.357 | 123.0444 | 14.52 | 0 | 0 | 0 | 1347938 |
| 99 | 4.822 | 123.0808 | 21.64 | 1631299 | 1918540 | 802955.5 | 1288081 |
| 100 | 6.23 | 123.11713 | 27.41 | 1009766 | 1649710 | 1623302 | 1547906 |

(4) The source-sink relationship is determined, and the receptor 1 and the receptor 2 are affected by the source water and a sewage outlet of the sewage treatment plant.

(5) A missing value in the dataset is corrected as 0, and the input matrix is standardized.

(6) A determined source-sink relationship, and information of substance-signal intensity in the HRMS dataset are input into an expectation-maximization source tracking method of R language, a quantitative contribution (percentage) of upstream source water and the pollution source to the receptor is obtained, see Table 4 for details.

TABLE 4

Contribution of upstream source water and pollution source to downstream water

| | Upstream | Pollution source | Unknown |
|---|---|---|---|
| Receptor 1 (sample 3) | 0.13424 | 0.73927 | 0.12649 |
| Receptor 2 (sample 4) | 0.85221 | 0.00598 | 0.14181 |

A conclusion is obtained, the receptor 1 is relatively close to the pollution source and is greatly affected by the pollution source, and a contribution of the pollution source to the receptor 1 is 73.9%; and the receptor 2 is far from the pollution source, and substances from the pollution source, after migration and degradation, have a small impact on the receptor 2, and the contribution of the pollution source to the receptor 2 is merely 0.60%.

Compared with the related art, beneficial effects of the disclosure at least include the follows.

(1) The HRMS is used to acquire pollution source chemical fingerprint, information of the pollution source chemical fingerprint is rich and accurate, which applies to pollution source apportionment of various environment mediums such as air, water and soil; (2) contributions of different pollution sources to the pollution receptor can be quantitatively evaluated by using multiple statistical algorithms.

More specifically, nontarget HRMS analysis technology used in the disclosure is an advanced technology for monitoring and analyzing the trace organic pollutants at present, which no need to identify detected substance, contribution of each pollution source can be quantitatively apportioned based on the nontarget HRMS data of known pollution sources and pollution receptors; information of the pollution source chemical fingerprint is complete and rich, which is beneficial for dealing with complex and diverse pollution sources.

The disclosure first proposes a quantitative method for contributions of the pollution sources based on the HRMS dataset in a field of environmental pollutant source apportionment, which can achieve a fast and accurate source apportionment under a situation that there are similar pollution source chemical fingerprint and a large number of potential pollution sources Finally, it should be noted that the above embodiments are merely used to illustrate the technical solution of the disclosure, not to limit it; although the disclosure has been described in detail concerning the aforementioned embodiments, those skilled in the art should understand that they can still modify the technical solutions recorded in the aforementioned embodiments, or equivalently replace some of the technical features; and these modifications or replacements do not separate the essence of the corresponding technical solutions from the spirit and scope of the various embodiments of the disclosure.

What is claimed is:

1. A quantitative source apportionment method based on nontarget high-resolution mass spectrometry (HRMS) data of pollution sources and pollution receptors, comprising:

step 1: acquiring samples of pollution sources and pollution receptors, and pre-processing the samples to extract trace organic pollutants;

step 2: acquiring nontarget HRMS data of the samples obtained in step 1;

step 3: performing data pre-processing on raw HRMS data obtained through nontarget analysis in step 2 to obtain a HRMS dataset comprising a mass-to-charge ratio, a retention time, and a peak area of substances;

step 4: determining source-sink relationship information based on positions of the pollution sources and the pollution receptors, taking each remaining sample other than a background sample and the samples of the pollution source as a sink sample, one sink sample corresponding to one group, and determining source samples of each sink sample;

step 5: constructing, based on the source-sink relationship information obtained in step 4 and the HRMS dataset obtained in step 3, an input matrix for each group of sink sample, and standardizing mass spectrometry data in the input matrix, comprising:

constructing a sink sample vector and a source sample vector for each group based on the mass spectrometry data obtained in step 3, representing a single sink sample by using a vector x, wherein a formula of x is $x=(x_1, \ldots, x_j, \ldots, x_N)$, $x_j$ represents a signal intensity of a j-th substance, N represents the number of all substance types in the HRMS dataset obtained in step 3; and representing a known source sample i of the sink sample x by using a vector $y_i$, wherein a formula of $y_i$ is $y_i=y_{i1}, \ldots, y_{ij}, \ldots, y_{iN}$, $y_{ij}$ represents a signal intensity of a j-th substance in the source sample i and $1 \leq i \leq K$, K represents the number of all known source samples of the sink sample x, and the sink sample x comprises a unknown source sample, that is a K+1-th source sample; and constructing the input matrix $(x^T, y_1^T, y_2^T, \ldots, y_K^T)$, where in a situation that the input matrix has a missing value, populating a value 0 into the input matrix; and standardizing the input matrix, comprising performing z-score standardization, a [0,1] standardization or a standardization of maximum and minimum values to obtain a standardized input matrix; and step 6: adopting an expectation-maximization method or a Bayesian method to quantitatively calculate contribution of each source sample based on the standardized input matrix, comprising one of:

substituting the vector x of the sink sample and the vector $y_i$ of the source sample i in the expectation-maximization method, comprising randomly assigning a value for contribution $\alpha_i$ of the sink sample x, and substituting the input matrix $(x^T, y_1^T, y_2^T, \ldots, y_K^T)$ in the expectation-maximization method to iterate the contribution $\alpha_i$ until convergence or reaching a maximum number of iterations; or substituting the vector x of the sink sample and the vector $y_i$ of the source sample i in the Bayesian method, comprising initializing the contribution $\alpha_i$ by using a random source environment assignment, iteratively calculating the contribution $\alpha_i$ to update each vector according to a conditional distribution, and calculating a posterior probability until convergence or reaching the maximum number of iterations;

wherein the quantitative source apportionment method further comprises: sending the contribution of each pollution source obtained from the step 6 to a sewage treatment manager, and developing, according to the contribution of each source, a sewage treatment scheme by the sewage treatment manager to perform sewage treatment, to enhance sewage treatment plant efficacy.

2. The quantitative source apportionment method based on nontarget HRMS data of pollution source and pollution receptor as claimed in claim 1, wherein step 1 comprises:

for an atmospheric particulate matter sample, acquiring the atmospheric particulate matter sample by using a large volume sampler and quartz fiber filter membranes, extracting non-polar organic compounds by using hexane and toluene and extracting polar organic compounds by using methanol and toluene to thus obtain an extract, and concentrating the extract under nitrogen gas;

for a water sample, extracting the water sample by using a composite solid-phase extraction (SPE) column comprising a lipophilic and hydrophilic balanced filler, a weak anion exchanger, a weak cation exchanger and a polar filler; sequentially eluting the composite SPE column by using neutral organic solution, acidic organic solution and alkaline organic solution to obtain an extract; and concentrating the extract under the nitrogen gas; and for a soil or sediment sample, sequentially performing an shaking extraction by using neutral organic solution, acidic organic solution and alkaline organic solution; extracting the soil or sediment sample by using the composite SPE column comprising the lipophilic and hydrophilic balanced filler, the weak anion exchanger, the weak cation exchanger and the polar filler; sequentially eluting the composite SPE column by using the neutral organic solution, the acidic organic solution and the alkaline organic solution to obtain an extract; and concentrating the extract under the nitrogen gas.

3. The quantitative source apportionment method based on nontarget HRMS data of pollution source and pollution receptor as claimed in claim 2, wherein step 2 comprises:

for the non-polar organic compounds, performing the nontarget analysis by using a gas chromatography (GC)-quadrupole time-of-flight HRMS with an electron ionization source or a chemical ionization source or a GC-Orbitrap HRMS with the electron ionization source or the chemical ionization source; and for the polar organic compounds and water-soluble compounds, performing the nontarget analysis by using an ultra-high-performance liquid chromatography (LC)-quadrupole time-of-flight HRMS with an electrospray ion source or an ultra-high-performance LC-Orbitrap HRMS with the electrospray ion source.

4. The quantitative source apportionment method based on nontarget HRMS data of pollution source and pollution receptor as claimed in claim 1, wherein step 3 comprises:

for a LC-HRMS, during performing peak extraction and peak alignment, setting a primary mass spectrometry (MS) permissible mass deviation and a secondary mass spectrometry ($MS^2$) permissible mass deviation, and extracting peaks of each sample within a range of permissible mass deviations for each MS and $MS^2$ to merge into one peak; and during performing peak elimination, setting a minimum extraction threshold and performing blank deduction, eliminating peaks with signal intensity smaller than the minimum extraction threshold and peaks existed in a blank sample.

5. A quantitative source apportionment method based on nontarget HRMS data of pollution sources and pollution receptors, comprising:

step 1: acquiring samples of pollution sources and pollution receptors, and pre-processing the samples to extract trace organic pollutants;

step 2: acquiring nontarget HRMS data of the samples obtained in step 1;

step 3: performing data pre-processing on raw HRMS data obtained through nontarget analysis in step 2 to obtain a HRMS dataset comprising a mass-to-charge ratio, a retention time, and a peak area of substances;

step 4: determining source-sink relationship information based on positions of the pollution sources and the pollution receptors, taking each remaining sample other than a background sample and the samples of the pollution source as a sink sample, one sink sample corresponding to one group, and determining source samples of each sink sample;

step 5: constructing, based on the source-sink relationship information obtained in step 4 and the HRMS dataset obtained in step 3, an input matrix for each group of sink sample, and standardizing mass spectrometry data in the input matrix, comprising:

constructing a sink sample vector and a source sample vector for each group based on the mass spectrometry data obtained in step 3, representing a single sink sample by using a vector x, wherein a formula of x is $x=(x_1, \ldots, x_j, \ldots, x_N)$, $x_j$ represents a signal intensity of a j-th substance, N represents the number of all substance types in the HRMS dataset obtained in step 3; and representing a known source sample i of the sink sample x by using a vector $y_i$, wherein a formula of $y_i$ is $y_i=y_{i1}, \ldots, y_{ij}, \ldots, y_{iN}$, $y_{ij}$ represents a signal intensity of a j-th substance in the source sample i and $1 \leq i \leq K$, K represents the number of all known source samples of the sink sample x, and the sink sample x comprises a unknown source sample, that is a K+1-th source sample; and constructing the input matrix $(x^T, y_1^T, y_2^T, \ldots, y_K^T)$, where in a situation that the input matrix has a missing value, populating a value 0 into the input matrix; and standardizing the input matrix, comprising performing z-score standardization, a [0,1] standardization or a standardization of maximum and minimum values to obtain a standardized input matrix; and step 6: adopting an expectation-maximization method or a Bayesian method to quantitatively calculate contribution of each source sample based on the standardized input matrix, comprising one of:

substituting the vector x of the sink sample and the vector $y_i$ of the source sample i in the expectation-maximization method, comprising randomly assigning a value for contribution $\alpha_i$ of the sink sample x, and substituting the input matrix $(x^T, y_1^T, y_2^T, \ldots, y_K^T)$ in the expectation-maximization method to iterate the contribution $\alpha_i$ until convergence or reaching a maximum number of iterations; or substituting the vector x of the sink sample and the vector $y_i$ of the source sample i in the Bayesian method, comprising initializing the contribution $\alpha_i$ by using a random source environment assignment, iteratively calculating the contribution $\alpha_i$ to update each vector according to a conditional distribution, and calculating a posterior probability until convergence or reaching the maximum number of iterations;

step 7: applying the contribution of each pollution source in pollution control and risk management of organic pollutants, to enhance sewage treatment plant efficacy.

* * * * *